United States Patent
Dahmen

(10) Patent No.: US 9,717,400 B2
(45) Date of Patent: Aug. 1, 2017

(54) ILLUMINATING LENS, OBSERVATION DEVICE AND METHOD FOR PRODUCING AN ILLUMINATING LIGHT BUNDLE

(71) Applicant: Karl Storz GmbH & Co. KG, Tuttlingen (DE)

(72) Inventor: Jan Dahmen, Seitingen-Oberflacht (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 334 days.

(21) Appl. No.: 13/677,525

(22) Filed: Nov. 15, 2012

(65) Prior Publication Data
US 2013/0121005 A1  May 16, 2013

(30) Foreign Application Priority Data
Nov. 15, 2011  (DE) .......... 10 2011 086 325

(51) Int. Cl.
*A61B 1/06* (2006.01)
*A61B 1/00* (2006.01)
(Continued)

(52) U.S. Cl.
CPC .......... *A61B 1/06* (2013.01); *A61B 1/0019* (2013.01); *A61B 1/00179* (2013.01); *A61B 1/0623* (2013.01); *A61B 1/0692* (2013.01); *F21L 15/14* (2013.01); *F21V 5/006* (2013.01); *G02B 3/14* (2013.01); *G02B 23/2461* (2013.01); *A61B 2090/306* (2016.02); *A61B 2090/309* (2016.02); *A61B 2090/502* (2016.02)

(58) Field of Classification Search
CPC .......... A61B 19/5223; A61B 19/5202; A61B 1/0692; A61B 1/0096; A61B 1/0638; A61B 5/0071; A61B 19/52; A61B 19/5212; A61B 1/063; A61B 1/07; A61B 1/06; G02B 25/00; G02B 25/02; G02B 25/007
USPC .............. 359/385, 388, 389, 376, 665–667; 600/101, 117, 118, 344; 362/105
See application file for complete search history.

(56) References Cited

U.S. PATENT DOCUMENTS 4,265,561 A * 5/1981 Heckele ................ A61B 19/26
                                                                362/105
4,529,264 A * 7/1985 Schmidt et al. ................ 385/31
(Continued)

FOREIGN PATENT DOCUMENTS

DE        3211187 A1   9/1983
DE    202007004527 U1   6/2007
(Continued)

OTHER PUBLICATIONS

German Search Report Application No. DE 10 2011 086 325.7 Date: Jul. 20, 2012 4 pages.

Primary Examiner — Darryl J Collins
Assistant Examiner — Journey Sumlar
(74) Attorney, Agent, or Firm — Whitmyer IP Group LLC

(57) ABSTRACT

An illuminating lens for a medical headlamp, endoscope or exoscope, to generate an illuminating light bundle with variable light distribution includes a liquid lens with variable focal length to modify a focusing of the illuminating light bundle. The invention also relates to an observation device with an illuminating lens of this type as well as a method to generate an illuminating light bundle with variable light distribution.

16 Claims, 4 Drawing Sheets

(51) Int. Cl.
*G02B 3/14* (2006.01)
*G02B 23/24* (2006.01)
*F21V 21/08* (2006.01)
*F21V 5/00* (2015.01)
*A61B 90/50* (2016.01)
*A61B 90/30* (2016.01)

(56) References Cited

U.S. PATENT DOCUMENTS

| | | | |
|---|---|---|---|
| 5,430,620 | A | 7/1995 | Li et al. |
| 7,314,300 | B1 | 1/2008 | Dorr et al. |
| 7,646,544 | B2 * | 1/2010 | Batchko .................. G02B 3/14 359/665 |
| 2006/0045504 | A1 * | 3/2006 | Zarnowski et al. ............ 396/79 |
| 2007/0156021 | A1 * | 7/2007 | Morse et al. ................. 600/167 |
| 2009/0177033 | A1 | 7/2009 | Hendriks et al. |
| 2010/0142059 | A1 * | 6/2010 | Chou ....................... G02B 3/14 359/666 |
| 2010/0309296 | A1 * | 12/2010 | Harrold et al. ................ 348/54 |
| 2012/0035422 | A1 * | 2/2012 | Lei et al. ..................... 600/173 |
| 2012/0113525 | A1 * | 5/2012 | Kong et al. .................. 359/665 |

FOREIGN PATENT DOCUMENTS

| | | |
|---|---|---|
| DE | 102009017801 A1 | 10/2010 |
| DE | 102009042906 A1 | 4/2011 |
| DE | 102011001200 A1 | 9/2011 |
| EP | 1747751 A2 * | 1/2007 |
| WO | 2007033326 A2 | 3/2007 |
| WO | 2007051173 A2 | 5/2007 |

* cited by examiner

ILLUMINATING LENS, OBSERVATION DEVICE AND METHOD FOR PRODUCING AN ILLUMINATING LIGHT BUNDLE

FIELD OF THE INVENTION

The present invention relates to an illuminating lens, in particular for a medical headlamp, an endoscope or exoscope, to an observation device, in particular a medical headlamp, an endoscope or exoscope, and in addition to a method for producing an illuminating light bundle with adjustable light dispersion.

BACKGROUND OF THE INVENTION

Medical headlamps include a carrier frame or a headband, with which an illumination unit can be carried on the user's head, as well as the illumination unit itself, which is carried above the user's eyes. The illumination unit can include a light source or an optic fiber by which the light generated from an external light source is transmitted into the illumination unit. The illumination unit comprises an illuminating lens through which the illuminating light generated from the light source or transmitted by the optic fiber is projected onto an object, such as onto a tissue surface, to illuminate an object field required for a medical investigation or for a surgical intervention. A medical headlamp can also be equipped with a viewing aid, such as binocular lenses, or else with a head-borne video camera.

In a medical investigation or a surgical intervention, it is desirable that the investigative or surgical site should be illuminated as homogeneously as possible with a strong light intensity sufficient for recognizing all details. The illuminated object area should be delineated with the sharpest possible edges so that as little illuminating light as possible is lost by illuminating areas outside the investigative or surgical site; in addition, thanks to sharply outlined demarcation of the illuminated object area, the entire heat development as well as the risk of glare affecting other persons is reduced.

In addition it can be necessary to illuminate object areas of various sizes and/or object areas in different working conditions. If the illuminating lens generates an illuminating bundle with a large opening angle, then a large object area can be illuminated. On the other hand, the light intensity can then be insufficient for recognizing details, especially at a relatively large working distance. If, on the other hand, the opening angle is small, then no doubt a sufficient illuminating intensity can still be achieved even at a fairly large working distance. In particular at a small working distance, the illuminated object area can, however, be too small for the intended investigation or operation. A sharp-edged delineation of the illuminated object area is desirable in each case, even at varying working distances.

Headlamps have therefore been developed that make it possible to modify the light distribution of a generated illuminating light bundle.

According to U.S. Pat. No. 5,430,620, a lens is placed before the outlet surface of an optic fiber, said lens being movable along the optical axis of the end portion of the optic fiber by means of a screw thread, so that the distance between the lens and the outlet surface of the optic fiber can be modified. This allows an adjustment of the size and brightness of the illuminated object area to the respective requirements, such that the outlet surface of the optic fiber is sharply configured only in the position of the greatest distance of the lens from the light-conducting surface. U.S. Pat. No. 7,314,300 B1 discloses a multi-lens illuminating lens system of a surgical headlamp in which the distance between a light-conducting surface and a convex lens can be modified by sliding a light-conducting attachment. This enables the light distribution in an illuminated object area to be modified. An adjustment to different working distances is not likewise foreseen as a result.

DE 32 11 187 A1 teaches how to axially slide a glass rod attached on a free end of a fiber optic light conductor, together with a diaphragm directly adjoining its light-radiating surface, with respect to a collector in order to sharply image the diaphragm into different working distances. As a result, an observation field situated in a pre-selectable plane can in each case be illuminated with sharp edges. The collector here can be configured as a vario system; such a system includes a number of lenses, which are slid with respect to one another, and it involves high manufacturing and adjustment expenditure.

Familiar from the prior art, the modification of the light distribution of an illuminating light bundle by mechanical adjustment of one or more lenses or of a light-conducting end causes an increased insulating expenditure because of the cleaning and sterilization requirements applicable in the medical field; this is especially true when the illuminating lens is part of a medical headlamp or is positioned in the distal end area of an endoscope or exoscope. An exoscope is understood to mean an observation device that is intended for use outside a cavity, such as is described in DE 10 2011 001 200 A1. Both an endoscope and an exoscope can include an illuminating lens to generate an illuminating light bundle, or a separate illumination unit with such an illuminating lens can be associated with an endoscope or an exoscope.

The aforementioned solutions for modifying the light distribution also result in an enlargement of the structural size and weight of the illumination unit, which is also not desired. Illuminating lenses, in which only one lens can be moved or one optic fiber end can be displaced with respect to a fixed lens arrangement, allow no independent adjustment of a focus and of a size of an illuminated object area at various working distances.

SUMMARY OF THE INVENTION

It is the object of the present invention to provide an illuminating lens, in particular for a medical headlamp, an endoscope or exoscope, for producing an illuminating light bundle with variable light distribution, as well as an observation device, in particular a medical headlamp, an endoscope or exoscope, and in addition a method for generating an illuminating light bundle with variable light distribution, such that the aforementioned disadvantages are avoided at least in part.

This object is achieved by providing an illuminating lens to generate an illuminating light bundle with variable light distribution characterized in that the illuminating lens includes a liquid lens with variable focal, an observation device with an illuminating lens to generate an illuminating light bundle with variable light distribution having a liquid lens with variable focal length to modify a focus of the illuminating light bundle, and a method of generating an illuminating light bundle with variable light distribution by running an illuminating light bundle through a liquid lens with a variable focal length.

Advantageous refinements of the invention can be seen from the dependent claims.

The invention relates to an illuminating lens for a medical headlamp, and an endoscope or exoscope that are in particular for medical use. A medical headlamp of this type can also include an observation device, in particular a video camera. An endoscope or exoscope of this type, in particular a medical endoscope or exoscope, can include an inventive illuminating lens; the illuminating lens can also be part of an illumination unit that is associated with the endoscope or exoscope yet separate from it.

The inventive illuminating lens is configured to generate an illuminating light bundle. In particular, the illuminating lens is configured to illuminate an object area by projecting the illuminating light generated from a light source onto the object area. The light source can be part of the headlamp or of the endoscope or exoscope, or else can constitute a unit separate from it, such that the illuminating light generated from the light source can be transmitted by means of an optic fiber, for example a beam of optic fiber fibers. To collect the greatest possible portion of the light generated from the light source and to conduct it to the illuminating lens, it is possible to provide, for instance, a switching lens for switching the light generated from the light source into the optic fiber or a collimator lens connected with a light source. The light source can be, for example, a xenon lamp or a light-emitting diode (LED) or an arrangement of LEDs. To generate the illuminating light bundle, the illuminating lens can comprise a lens arrangement that can include one or more lenses as well as, in some cases, additional optical elements such as mirrors and/or diaphragms.

The inventive illuminating lens is configured to generate an illuminating light bundle with variable light distribution. In particular, the opening angle of the illuminating light bundle, which is also referred to as the angle of illumination, and/or the light intensity decline in the peripheral area of the illuminating light bundle can be variable. It is also possible to modify other properties of the light distribution, such as the homogeneity of the illumination of an object field. The brightness distribution within an illuminated object field can depend on the distance of the object field from the illuminating lens.

According to the invention, the illuminating lens comprises a liquid lens whose focal length can be modified to vary a focus of the illuminating light bundle. By modifying the focal length of the liquid lens, a convergence or divergence of bundles of the illuminating light bundle is thereby variable. In particular, the convergence or divergence of bundles, which emanate from a point of a light source or of an end surface of an optic fiber, can be modified. In addition, other properties of the light distribution, such as the opening angle of the illuminating light bundle, can be modified by this means. The illuminating lens can comprise a lens arrangement that includes the liquid lens with variable focal length.

Because the illuminating lens comprises a liquid lens with variable focal length for modifying a focus of the light bundle, it is a simple matter to modify the light distribution of the illuminating light bundle generated by the illuminating lens. In particular when the illuminating lens comprises no additional imaging optical element, in particular no additional lens than the liquid lens with variable focal length, it is possible to achieve an especially simple structure of the illuminating lens. Consequently, it becomes possible to produce the illuminating lens with an especially small structural space and an especially small weight. In addition, to modify the focal length of the liquid lens, as a rule no mechanical sliding of an optical element is required, so that the insulation of the illuminating lens or of an illumination unit that includes the illuminating lens is simplified.

According to a preferred embodiment of the invention, the focal length of the liquid lens is electrically adjustable. In particular, the focal length of the liquid lens can be modified by an electric current that generates an electric field that, by means of the effect of the electrical network, controls the contact angle of a liquid contained in the liquid lens and thus the curvature of the optically effective border surface. The adjustment of electric current can occur, for example, by a pushbutton or other service element that is associated with the illumination unit or attached on it. Because the focal length of the liquid lens is electrically modifiable, a particularly diverse powering of the liquid lens becomes possible for changing the light distribution of the illuminating bundle. In addition, a construction without mechanically moveable elements and thereby an especially simple structure of the illumination unit become possible, such that no additional actions are necessary for insulation.

Alternatively or in addition, an adjustment of the focal length of the liquid lens can occur by mechanical means. Thus the liquid lens can, for example, comprise a sleeve into which the liquids are received that form an optically effective border surface and whose radius is mechanically modifiable. Preferably the illuminating lens or the illumination unit includes a mechanical service element, in particular a rotary wheel, that acts on the liquid lens directly or, for example, by a gear wheel, to modify the focal length. As a result, with an easily useable operating element and with a comparatively simple structure of the illuminating lens, a modification of the light distribution of the illuminating light bundle becomes possible, such that the insulation requires only relatively minor expenditure.

In addition it is preferred that the illuminating lens should be configured by adjusting different focal lengths of the liquid lens to obtain sharp-edged illumination of an object area at different working distances. Because the lens arrangement includes a liquid lens with variable focal length, sharp-edged illumination of an object field becomes possible at different working distances with an especially simple optical and mechanical structure of the illuminating lens. This is especially true in the event that the lens arrangement comprises no additional lenses beyond the liquid lens.

In particular, the illuminating lens is configured to image a light outlet surface onto the object area. For example, the liquid lens can be positioned in such a way that the light outlet plane coincides with a focal plane that corresponds to a focal length in a first adjustment of the liquid lens, such that to image the light outlet plane onto the object area, the focal length can be reduced with respect to the first adjustment. A sharp imaging of the light outlet plane onto the object area allows in particular a sharp outlining of the illuminated surface. Because of the imaging of the light outlet plane onto the object area, the latter can be especially homogeneously and sharply illuminated.

The light outlet plane can, in particular, be the plane of a diaphragm, of an outlet surface of an optic fiber, or else of a diffusing panel. In particular when the light source is part of the medical headlamp or of the endoscope or exoscope, a diaphragm constitutes an advantageous possibility for restricting the illuminating object area. For further improvement of the homogeneity of the illumination of the object area, a diffusing panel can also be foreseen in the light outlet plane. The diaphragm or diffusing panel can be part of the illuminating lens. In the event that the light source is positioned separately and the illuminating light is transmitted via an optic fiber to the illuminating lens, the light inlet plane is in particular the end surface of the optic fiber. This can be a surface in which the end surfaces of the optic fiber fibers are positioned.

While in theory an imaging of the light outlet plane onto the object area is desirable to generate a sharp boundary of the illuminated area, a slightly un-focused imaging of the light outlet plane is especially advantageous. As a result, for example in imaging a light-conducting end surface onto the object area, it becomes possible to prevent a non-homogeneous illumination of the light-conducting end surface from causing a non-homogeneous illumination of the object area as a result of the dark intermediate areas between the light-conducting fibers. In addition, in this manner, it becomes possible to achieve a homogeneous illumination of the object area partially without losses of light. The sharp outlining of the illuminated object area is consequently reduced only partially or in a manner completely imperceptible to the user. In the present application any reference to the terms "sharp" or "sharp outlined" therefore includes an almost sharp, that is only slightly unfocused, illumination or imaging.

According to a preferred embodiment of the invention, the illuminating lens is configured to modify an opening angle of the illuminating light bundle. The illuminating light can thus be projected onto the object area at varying angles of illumination. The illuminating light is projected onto the object area, for example, in the form of a light cone, such that the angle of illumination indicates the opening angle of the light bundle or the angular diameter of the cone. The angle of illumination can be of different sizes in different directions; reference is made hereinafter, in this case as well, to "the angle of illumination" for the sake of simplicity. In this way it becomes possible to illuminate an object area that can be adjusted to a desired size, regardless of the distance of the object area from the illuminating lens.

In preferred manner, the liquid lens is mounted so that it can be moved, in particular by sliding, along an optical axis of the illuminating lens. To move or slide the liquid lens, a mechanical or electro-mechanical power drive can be provided. By sliding the liquid along the optical axis and by adjusting the focal length of the fluid lens, it becomes possible in an especially simple manner to illuminate an object area of a particular desired size with the object area at different distances from the illuminating lens. In particular, no additional lens besides the liquid lens is required, in particular; it is also possible to provide a lens arrangement, which can include additional lenses or optically effective surfaces.

In especially preferred manner, the adjustment of the focal length of the liquid lens and the sliding of the liquid lens along the optical axis of the lens arrangement are coupled together in such a way that at a fixed working distance, object areas of different size can each be illuminated with a sharp outline. It is also possible to provide, for example, that the adjustment of the focal length and the sliding of the liquid lens are coupled together in such a way that an object area of predeterminable size is illuminated with a sharp outline in each case at different distances to the illuminating lens. In the way, an especially simple operation of the illuminating lens becomes possible in important fields of application.

In particular in the event that the focal length of the liquid lens can be modified by mechanical means, the movement of the liquid lens along the optical axis, coupled with the adjustment of the focal length, is preferably mechanically coupled with a mechanical operating element. Thus, for example, a sliding motion of the liquid lens by a screw drive can be coupled with the rotation of a rotary wheel, which can be actuated to modify the focal length of the liquid lens. If the focal length of the liquid lens is electrically adjustable, a sliding of the liquid lens along the optical axis of the illuminating lens can also be actuated electrically, in particular electro-mechanically. In especially advantageous manner, the illuminating lens can be connected with an electronic control, both to adjust the focal length of the liquid lens and to move the liquid lens along the optical axis. As a result, in a manner that is both especially comfortable and flexible in its applications, it becomes possible to modify the focal length of the liquid lens, to slide it along the optical axis, and to couple both adjustment possibilities.

An inventive observation device, which is preferably a medical observation device, in particular a medical headlamp with a video camera device, endoscope or exoscope, comprises an illuminating lens of the aforementioned type. At the same time, the illuminating lens can be integrated into the illumination device or can be associated with it as part of a separate illumination unit. In addition, the illumination device comprises an observation lens, which can be, for example, a video camera lens or a lens with an image transmitter, for example a relay lens system or an image conductor. As a result, an observation device, especially a medical headlamp with observation device or endoscope or exoscope, is provided in which the light distribution of an illuminating light bundle can be modified in simple manner. As a result, in particular, a sharp-edged illumination of an object area becomes possible at different working distances by adjustment of the focal length of the fluid lens.

According to a preferred embodiment, the observation device comprises an observation lens with a variable lateral angle, for example a zoom lens of a video camera, and the illuminating lens is configured to adjust an angle of illumination to the variable viewing angle. The observation device can be, for example, a headlamp with a video camera device with a zoom lens, or a viewing aid with variable enlargement; also with endoscopes or exoscopes it is a known process to modify the visual field by means of a zoom lens. As a result, it becomes possible in simple and effective manner, at different viewing angles, always to select an optimal and flexible illumination of an object field, in particular a complete and sufficiently bright illumination of an object field. As a result, in particular, the object area that can be illuminated with sharp edges can be adjusted to a selected enlargement of the observation device.

According to a preferred embodiment of the invention, the fluid lens can be powered to adjust the focal length of an electronic control device. An electronic control device of this type, with a medical headlamp with observation device or with an endoscope or exoscope, can be provided for example to power a video camera, a light source or other functions. Because the liquid lens can be powered by the electronic control device, it becomes possible, for example, to adjust the focal length according to commands entered by a user via an input device such as voice command, or else to automatically focus by means of electronic control and thus to ensure an especially simple and secure operation. In addition, sterility problems can be avoided because no touching of the illuminating lens is necessary in order to adjust the illuminating lens.

In the event that the liquid lens is movable along an optical axis of the lens arrangement, it is also possible to foresee powering of the movement or sliding of the liquid lens by electronic control, such as by powering of an electro-mechanical adjusting element. As a result, in especially advantageous manner, the movement of the liquid lens along the optical axis can be coupled with the adjustment of the focal length of the liquid lens, so that, for example, adjustment of an angle of illumination and focus of the illuminating lens become possible, depending on the working distance. In particular, the electronic control device can be configured to record the viewing angle and to automatically adjust the illuminating lens to adapt the angle of illumination to the viewing angle. In the process, the angle of illumination can be selected as especially slightly larger than the viewing angle in order to avoid darkening in the peripheral range of the visual field of the observation device, such as would be caused by a misalignment between the observation device and the illuminating lens or by a lack of sharp edges of the illuminated area. As a result, a particularly simple and secure operation becomes possible.

In an inventive method to generate an illuminating light bundle with variable light distribution, a liquid lens with variable focal length is used in order to modify the light distribution of the illuminating light bundle. In particular, by a modification of the focal length of the liquid lens, the focus of the illuminating light bundle can be modified. An illuminating lens that generates the illuminating light bundle to illuminate an object area can comprise a lens arrangement that includes the liquid lens with variable focal length and can include additional optical elements. As a result, in especially simple and effective manner, an illuminating light bundle with variable light distribution can be generated.

In particular, the illuminating lens described above and the described observation device is suited for performing the inventive method.

It is understood that the aforementioned features and those yet to be described are applicable not only in the combination indicated in each case but also in other combinations or individually, without departing from the framework of the present invention.

BRIEF DESCRIPTION OF THE DRAWINGS

Further aspects of the invention can be seen from the following description of a preferred embodiment and from the appended drawings, which are as follows.

DETAILED DESCRIPTION OF THE INVENTION

Figure 1:
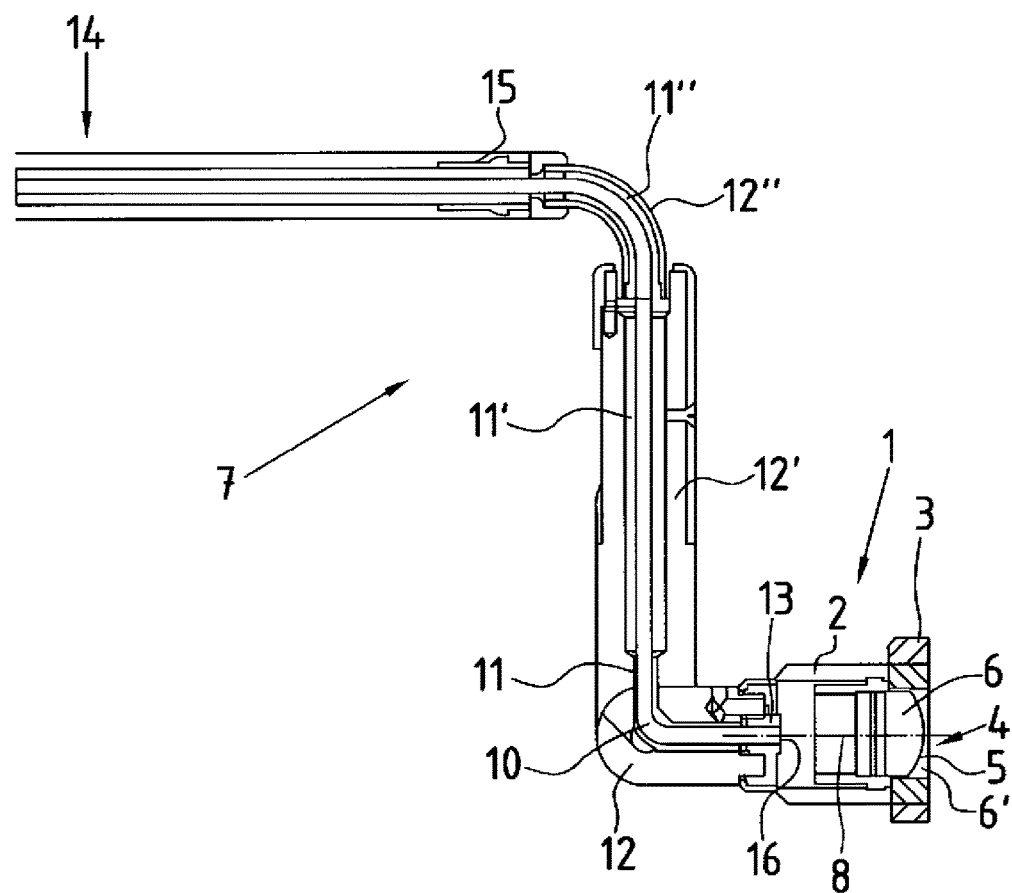
FIG. 1 shows an illumination unit of a headlamp according to a first embodiment of the invention, in a schematic longitudinal section.

As is shown schematically in FIG. 1, an illuminating lens 1 according to an embodiment of the invention includes an essentially cylindrical sleeve 2 on whose outside in its distal end portion a manually adjustable rotary wheel 3 is positioned. Positioned inside the rotary wheel 3 and inside the sleeve 2 is a liquid lens 4, which comprises a border surface 5 between two liquid or gel-type optical media 6, 6', and which in the illustrated example acts as a converging lens (corresponding to a convex lens). In the illustrated embodiment, the liquid lens 4 constitutes the only optically effective surface of the illuminating lens 1. However, still other optical elements, in particular other lenses, can be positioned inside the sleeve 2; in this case the liquid lens 4 can also be configured or adjustable to act as a diffusing lens (corresponding to a concave lens).

The illumination unit 7 of a medical headlamp also includes an optic fiber 10, which for example consists of a beam of light-conducting fibers. The optic fiber 10 is enclosed by a sleeve 11, 11', 11" and is guided by control elements 12, 12', 12" into the illuminating lens 1. While the distal end of the optic fiber is held centered to the optical axis 8 of the illuminating lens 1 by a light-conducting frame 13, the proximal end of the optic fiber leads into a light-conducting cable 14, which can be connected with an external light source. The light-conducting cable is protected by a kink guard 15 on the extension of the control element 12".

To illuminate an object area, in an external light source that is not shown in FIG. 1, such as a xenon light source, light is switched into the optic fiber 10. This light emerges from the optic fiber 10 at its distal end surface 16 and is projected by the liquid lens 4 onto an object area. The fluid lens 4 is positioned at a fixed distance from the distal end surface 16 of the optic fiber 10. By rotating the rotary wheel 3, it is possible to modify the radius of a slave of the liquid lens 4, which contains the optical media 6, 6'. As a result, the curvature of the border surface 5 and thus the focal length of the liquid lens 4 are modified. In this way the focus of the light bundle indicated by the illuminating lens can be adjusted in such a way that object areas at different working distances can each be illuminated with sharp edges. A loss of light by illuminating unnecessary areas of an object can be avoided in this way. Other optical elements can be positioned inside the sleeve 2, in particular to converge the light emerging from the distal end surface 16 of the optic fiber 10 and thus to avoid loss of light as well as to improve homogeneity of illumination within the illuminating light cone.

Figure 2:
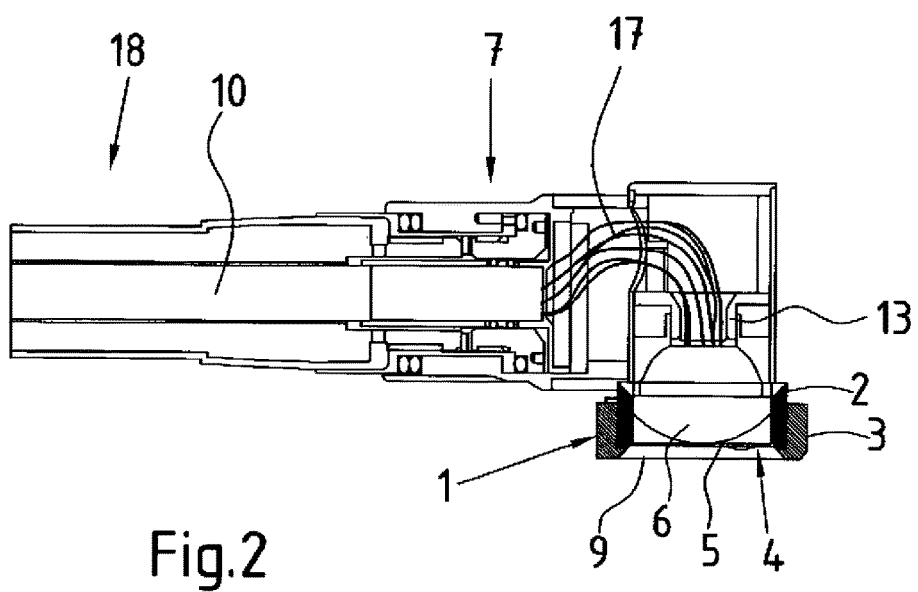
FIG. 2 shows a separate illuminating unit for an endoscope or exoscope with an illuminating lens according to a second embodiment of the invention, in a schematic partial section.

FIG. 2 shows an additional embodiment of an illuminating lens, such that corresponding elements are designated with the same reference numbers as in FIG. 1. The illuminating lens 1 includes a sleeve 2 on which a rotary wheel 3 is rotatably mounted in order to adjust the focal length of a liquid lens 4 positioned rigidly inside the sleeve 2. The sleeve 2 further comprises a cover glass 9, which is connected with the sleeve 2 in insulated manner. The optic fiber 10 includes a beam of symbolically illustrated light-conducting fibers 17, which lead into a light-conducting frame 13 with which they are held in the illuminating lens 1. The illumination unit 7 depicted in FIG. 2 is, in particular, conceived as a separate illumination unit for an exoscope and for this purpose can comprise an adjustable swan's neck 18. The illumination unit 7, however, can also be coupled with an exoscope or endoscope or can be integrated into one of these.

Figure 3:
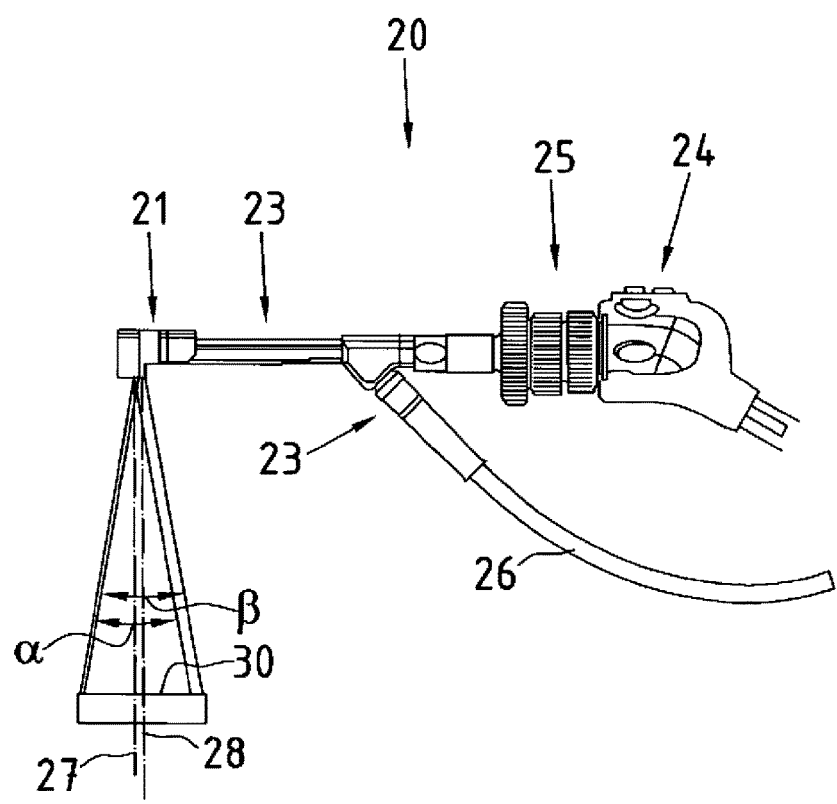
FIG. 3 shows an exoscope with an integrated illuminating unit, in a side view.

An endoscope with an illumination unit is shown in FIG. 3. In the distal end area 21 of the exoscope 20, an illuminating lens is integrated that is configured according to an additional embodiment and that is supplied with the illuminating light generated by an external illumination unit via a light-conducting cable 22 and light-conducting fibers that are fed into a shaft 23 of the exoscope 20. The illuminating lens generates a light cone with an opening angle $\alpha$, which is also designated as the angle of illumination.

The distal end area 21 of the exoscope 20 also contains a lens of an image recording device that can be configured in particular as a zoom lens. The exoscope 20 thereby makes it possible to observe an object at a changeable viewing angle β. Light captured by the lens is transmitted by an image transmitter contained in the shaft 23, for example rod lenses or an arranged beam of light-conducting fibers, to a video camera situated in the head 24 of the exoscope. The video camera can also be positioned in the distal end area 21 of the exoscope in miniaturized form. The head 24 of the exoscope is connected with the shaft 23 by a coupling 25. The light-conducting cable 22 is also dissolubly connected with the shaft 23 by a coupling 26.

As is schematically shown in FIG. 3, the angle of illumination a is selected in such a way that it corresponds essentially with a viewing angle β of the video camera, which can be modified by the zoom lens. The slight misalignment of, for example, a few millimeters between the optical axis 27 of the illuminating lens and the optical axis 28 of the observation lens is, in particular, negligible for the illumination of the object area 30 when the latter is at a distance from the distal end area 21 of the exoscope that is markedly greater than the misalignment, that is, for example, a distance of a few centimeters. The angle of illumination a can be selected, in particular, as slightly greater than the viewing angle R, so that in any case a complete illumination of the object area 30 is achieved at all desired working distances. By axial sliding of the liquid lens, the angle of illumination a can be modified in such a way that it is always adjusted to the viewing angle β of the video camera that can be modified with the help of the zoom lens. By modifying the focal length of the liquid lens, focus is achieved so that the illumination of the object area 30 occurs with a sharply defined border. As a result, in every possible enlargement that is selected by adjusting the zoom lens, an optimal sharply outlined illumination of the viewing field is always achieved. By means of an electronic control device not shown in the illustration, the viewing angle β of the observation lens and possibly also a distance between the distal end area 21 of the exoscope and the object area can be recorded and the sliding of the liquid lens as well as the adjustment of the focal length of the liquid lens can be automatically controlled in such a way that the viewing field of the observation lens is always completely illuminated and the smallest possible portion of the illuminating light illuminates areas outside the viewing field and the illuminated object field is always sharply outlined. The bundle path of the illuminating lens is clarified by way of example by referring to FIGS. 4 and 5.

Figure 4:
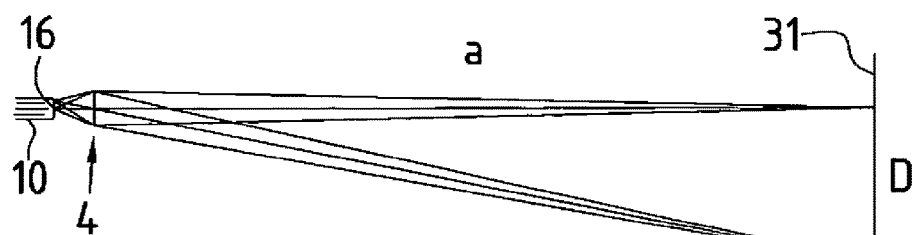
FIG. 4 shows a schematic depiction of the bundle path of an embodiment of an inventive illuminating lens with a first object field diameter.
Figure 5:
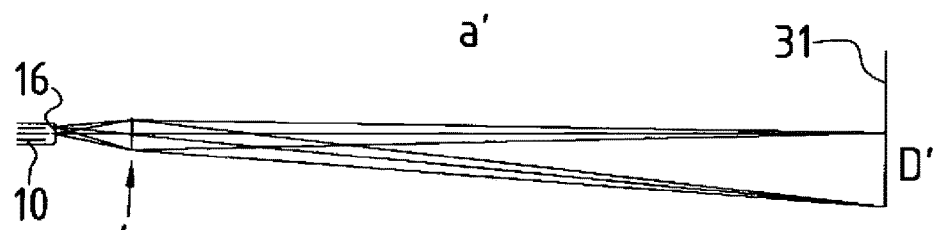
FIG. 5 shows a schematic depiction of the bundle path of the embodiment from FIG. 4 with a second object field diameter.

As shown schematically in FIGS. 4 and 5, the illuminating light emanating from a distal end surface 16 of an optic fiber 10 is imaged by a liquid lens 4 into an object plane 31, so that an image of the end surface 16 of the optic fiber appears in the object plane 31 with an image radius R. In the arrangement shown in FIG. 4, the liquid lens 4 is adjusted to a relatively short focal length, for example to a focal length of 12.5 mm, so that, with the object plane 30 at a distance a=250 mm from the liquid lens 4, an illuminated surface emerges with a diameter D=10 mm.

According to FIG. 5, the liquid lens 4 can be adjusted to a greater focal length of, for example, 25 mm. In this case, an image of the end surface of the optic fiber with a diameter D'=5 mm appears in the object plane 31, which again can be at a distance a'=a=250 mm from the liquid lens 4. The distance of the liquid lens 4 from the end surface 16 of the image conductor 10, corresponding to the enlargement of the focal length of the liquid lens 4 in FIG. 5 with respect to the arrangement in FIG. 4, is enlarged from approximately 12.5 mm to about 25 mm.

Because of an adjustment of the focal length and an axial sliding of the liquid lens corresponding to a modified focal length of the video camera or of the observation lens, it is possible to adjust the diameter of the illuminated object area, which corresponds here to the diameter D or D' of the image of the light-conducting surface 16. The object area here can be all the more brightly illuminated, the smaller the diameter is selected. Thus, for example, if no losses of light occur, the surface brightness of the illuminated area in FIG. 5 can be four times as great as in FIG. 4. By coupling an electric signal of the zoom lens of the video camera with an electrically powered liquid lens, it is thus possible at every selected enlargement to receive a homogeneous, equally strongly illuminated image.

In FIGS. 4 and 5, for the sake of simplicity, a focus on the object plane 31 is shown; however, a slightly non-focused imaging can be advantageous to improve homogeneity of the illumination of the object area.

For a clearer overview, not all reference numbers are shown in all images. Those reference numbers not explained in a drawing have the same significance as in the other drawings.

What is claimed is:

1. An illuminating lens for a medical headlamp, the illuminating lens configured to generate an illuminating light bundle with variable light distribution, the illuminating lens comprising:
    a liquid lens with variable focal length to modify a focus of the illuminating light bundle; and
    an annulus configured to directly modify the focal length of the liquid lens;
    wherein the annulus extends circumferentially around the liquid lens, and the annulus is configured such that rotation of the annulus about an optical axis of the illuminating lens modifies a radius of a sleeve of the liquid lens, and thereby modifies the focal length of the liquid lens, the radius of the sleeve defined in a direction perpendicular to the optical axis of the illuminating lens.

2. The illuminating lens according to claim 1, wherein the illuminating lens is configured for sharp-edged illumination of an object area at different working distances by adjusting different focal lengths of the liquid lens.

3. The illuminating lens according to claim 2, wherein the illuminating lens is configured to image a light outlet plane onto the object area.

4. The illuminating lens according to claim 1, wherein the illuminating lens is configured to modify an opening angle of the illuminating light bundle.

5. The illuminating lens according to claim 4, wherein the liquid lens can be slid along the optical axis of the illuminating lens.

6. The illuminating lens according to claim 5, wherein a modification of the focal length and a sliding of the liquid lens are coupled with one another.

7. The illuminating lens according to claim 1, wherein the liquid lens is the only optically effective surface of the illuminating lens.

8. The illuminating lens according to claim 1, wherein the liquid lens is a converging lens.

9. The illuminating lens according to claim 1, wherein the annulus is a rotatable wheel.

10. A medical headlamp with an illuminating lens to generate an illuminating light bundle with variable light distribution, comprising:
- a liquid lens with variable focal length to modify a focus of the illuminating light bundle; and
- an annulus configured to modify the focal length of the liquid lens directly;
- wherein the annulus extends circumferentially around the liquid lens, and the annulus is configured such that rotation of the annulus about an optical axis of the illuminating lens modifies a radius of a sleeve of the liquid lens, and thereby modifies the focal length of the liquid lens, the radius of the sleeve defined in a direction perpendicular to the optical axis of the illuminating lens.

11. The medical headlamp according to claim 10, wherein the observation device comprises an observation lens with a variable viewing angle and the illuminating lens is configured to adjust an angle of illumination to the viewing angle.

12. The medical headlamp according to claim 10, wherein the liquid lens can be powered to adjust the focal length of an electronic control device.

13. The medical headlamp according to claim 12, wherein the electronic control device is configured to adjust the angle of illumination to the viewing angle.

14. The medical headlamp according to claim 10, wherein the annulus is a rotatable wheel.

15. A method to generate an illuminating light bundle with variable light distribution from an illuminating lens of a medical headlamp, comprising:
- running an illuminating light bundle through a liquid lens with a variable focal length;
    - directly modifying a radius of a sleeve of the liquid lens, and thereby modifying the focal length of the liquid lens, by rotating an annulus that extends circumferentially around the liquid lens about an optical axis of the illuminating lens, the radius of the sleeve defined in a direction perpendicular to the optical axis of the illuminating lens.

16. The method according to claim 15, wherein the annulus is a rotatable wheel.

* * * * *